US00PP28487P2

(12) United States Plant Patent
Hansen

(10) Patent No.: US PP28,487 P2
(45) Date of Patent: Oct. 3, 2017

(54) ***PHLOX* PLANT NAMED 'AMETHYST PEARL'**

(50) Latin Name: ***Phlox* hybrid**
Varietal Denomination: Amethyst Pearl

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/330,047

(22) Filed: Jul. 29, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para

(57) ABSTRACT

A new and unique cultivar of garden *phlox* named *Phlox* 'Amethyst Pearl' multi-stemmed compact habit, slowly spread plant with bright, glossy-green, lanceolate leaves. Flowers are sweetly fragrant, light lavender-pink with white eye beginning very early in early June, continuing for about four weeks and repeating in early-fall. Foliage stays clean and resists mildew.

1 Drawing Sheet

Botanical classification: *Phlox* hybrid.
Variety denomination: 'Amethyst Pearl'.

BACKGROUND OF THE INVENTION

The present invention relates to a new and distinct cultivar of *Phlox* plant, known as *Phlox* 'Amethyst Pearl' and will be referred to hereafter by its cultivar name, 'Amethyst Pearl', or the "new plant". The new plant was discovered in a production field of a wholesale perennial nursery in Zeeland, Mich. on Oct. 11, 2011 as an non-induced branch sport on *Phlox* 'Minnie Pearl' and assigned the temporary accession number of 11-SP-PHL-101. 'Minnie Pearl' was originally found along a roadside in Kemper, Miss. in a natural population presumed to be a natural hybrid between *Phlox maculata* and *Phlox glaberrima*. The new plant has been asexually propagated by stem cuttings in the greenhouses at the same nursery in Zeeland, Mich. The unique characteristics of the new plant have been found to be reproducible and stable in successive generations of asexually propagated and the resultant plants have been found to be identical to the original selection.

No plants of *Phlox* 'Amethyst Pearl' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

*Phlox* 'Amethyst Pearl' is unique from all other tall garden *phlox* or other *phlox* known to the inventor. The new plant differs from 'Minnie Pearl' by having light lavender pink flowers with a white eye compared to the solid white flower of 'Minnie Pearl'. Compared to other known *Phlox paniculata* hybrids 'Amethyst Pearl' has foliage of stiffer and thicker-substance and the flowers about a month earlier.

'Amethyst Pearl' differs from and all other *phlox* known to the inventor in the following repeatedly observed traits in combination:

1. Plants of compact habit, slowly spreading by short rhizomes, producing clean, glossy, bright-green, lanceolate leaves.
2. Foliage thicker substance than *Phlox paniculata* types.
3. Multiple stems produce rounded heads of flower very early in the season.
4. Sweetly fragrant flowers on stems of about 30 to 45 cm tall producing sweetly-fragrant light lavender-pink flowers with white eye zones.

BRIEF DESCRIPTION OF THE DRAWINGS

The photographs of the new plant demonstrate the unique traits of 'Amethyst Pearl' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
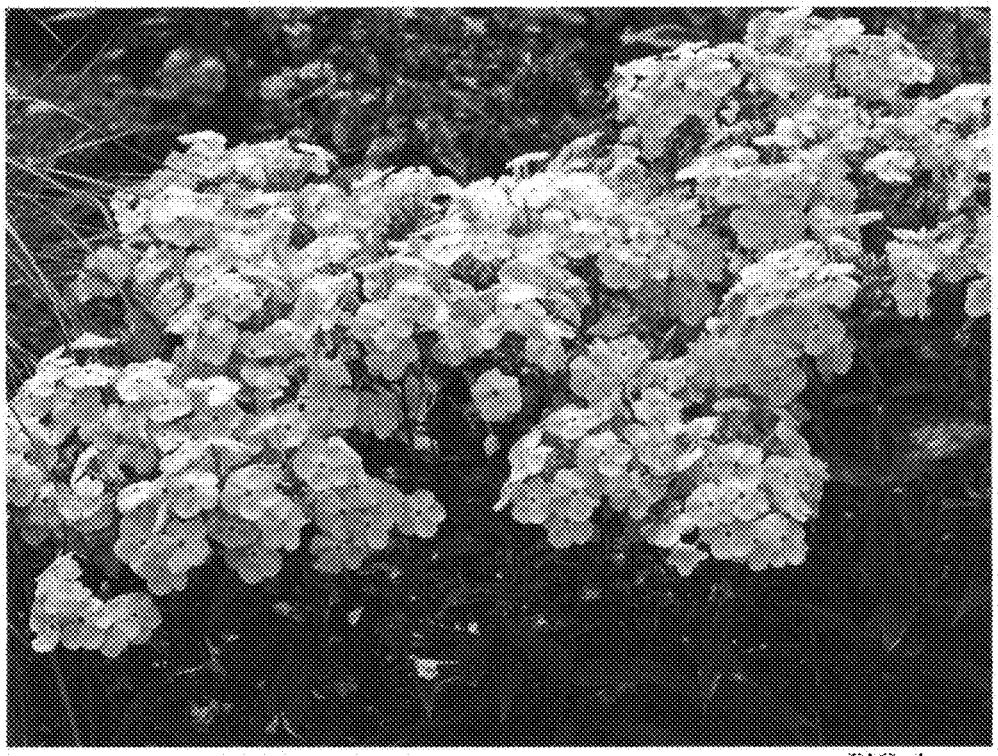
FIG. 1 shows the new plant in flower in the landscape with late spring to early summer foliage.
Figure 2:
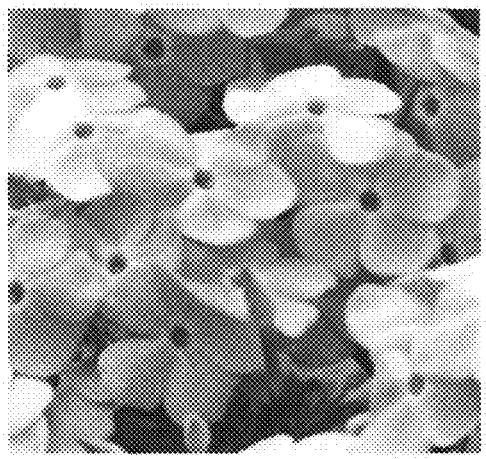
FIG. 2 shows the floriferous flower head of the new plant together with mid-summer foliage.

The following descriptions and color references are based on The 2001 edition of The Royal Horticultural Society Colour Chart except where common dictionary terms are used. *Phlox* 'Amethyst Pearl' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid.

Parentage: Non-induced branch sport mutation of *Phlox* 'Minnie Pearl'.

Plant habit: Hardy herbaceous perennial, compact, producing about 30 to 40 rigid upright stems; 30 to 45 cm tall at flowering and 26 to 33 cm wide; rounded panicle cluster about 9.0 cm across and 7.0 cm tall; flowering begins about June 8th in Michigan and continuing for about 4 weeks and repeating in the early-fall if deadheaded for another 3 weeks.

Propagation: Stem cuttings; rooting in about 14 days.

Time to produce finished crop in 3.8 liter pots: About 8 to 10 weeks; moderate rate of growth.

Root: Primary roots to about 1.0 mm thick; secondary fibrous and freely branching; color creamy white to tan depending on soil type.

Leaves: Simple, opposite, lanceolate, entire; slightly puberulent adaxial surrounding vein and glabrous abaxial; lustrous adaxial, matte abaxial; acute apex, rounded base; about 11.0 cm long by about 1.9 cm wide near the center.

Leaf color at flowering: Adaxial nearest RHS 137A; abaxial surface nearest RHS 147C.

Foliage fragrance: None detected.

Veins: Pinnate; glabrous abaxial, slightly puberulent adaxial; mid-vein about 1.0 mm wide at base, slightly sunken adaxial and raised abaxial.

Vein color: Adaxial midrib between RHS 163B and RHS 162A, nearest RHS 145C on abaxial surface; secondary veins same color as surround leaf.

Petiole: Leaves sessile.

Stems: Terete; stiff; strong; upright; glabrous to minutely puberulent; about 26.0 cm long and 3.0 mm diameter at base.

Stem color: Between RHS 145B and RHS 145C distally becoming more maculate proximally with lowest 4.0 cm nearest solid RHS 83B.

Nodes: About 9 per stem; average internode length about 2.9 cm; shorter proximally and longer distally.

Node color: Between RHS 145B and RHS 145C.

Flowers: Perfect; salverform, with fused tube about 2.8 cm long and face about 2.8 cm across consisting five petals; held in a tight panicle of about 48 flowers; attitude upright to outward.

Flower longevity: About 5 days on plant or as cut flower; self-cleaning.

Flower fragrance: Pleasantly sweet.

Buds one to two days prior to opening: Narrowly oblanceolate, to nearly clavate; acute apex with petals twisted about each other; about 3.3 cm long and 1.5 mm diameter in tube and 4.0 mm diameter toward apex.

Bud color: Nearest RHS 76C distally with tube nearest RHS N77D distally and nearest RHS 150D.

Petals: Five, glabrous except for adaxial about 10.0 mm of tube throat, rounded limbs with rounded to emarginate apex; limbs diameter about 1.2 cm, overlapping about one-third of the petals to either side; base fused into a tube about 3.0 mm diameter and 2.6 cm long; basal one-third of tube inner surface with fine hairs the same color as petals.

Petal color:

*Top or adaxial surface of limb.*—Central eye of about 5.0 mm diameter nearest RHS 155D, remainder of petal outside of center eye of nearest RHS 84B.

*Back or abaxial surface of limb.*—Between RHS 76B and RHS 76C.

*Inner or adaxial surface of tube.*—Between RHS 75C and RHS 75D in dorsal half and gradually lightening to nearest RHS 150D at base.

*Outer or abaxial surface of tube.*—Between RHS 75C and RHS 75D in dorsal half and lightening to lighter than RHS 150D at base.

Androecium:

*Filaments.*—Usually five, fused to inner petals, of varying lengths between 1.0 mm and 2.0 mm and less than 0.5 mm in diameter; lighter than RHS 155D.

*Anther.*—Oblong elliptic; dorsifixed; oblong, about 2.5 mm long by 0.5 mm wide.

*Anther color.*—Nearest RHS 17B.

*Pollen.*—Nearly microscopic, spherical; color nearest RHS 17B.

Gynoecium: One pistil per flower.

*Style.*—Cylindrical; about 2.8 cm long and 0.5 mm diameter when flower is mature; lighter than RHS 1D and more yellow-green than RHS 155C in the center and distal portion and near white lighter than RHS 155D at base.

*Stigma.*—Split into three branches in the proximal 2 mm, less than 0.25 mm in diameter; persistent after flower abscission; nearest RHS 2C.

*Ovary.*—Inferior; elliptic, about 2.0 mm long and1.0 mm diameter; color nearest RHS 145A.

Sepals: Five, glabrous; lanceolate; acute apex, fused in basal 7.0 mm; individually about 10.0 mm long and 1.0 mm wide.

Sepal color: Between RHS 137B and RHS 139B on both adaxial and abaxial surfaces with heavy tinting of between RHS 187A and RHS N187A.

Peduncle: Glaucous to minutely puberulent, stiff, strong, upright, terete; about 1.5 mm diameter at base and 4.0 cm long; branched at distal nodes.

Peduncle color: Blend between RHS 151A and RHS 151B.

Fruit: Dehiscent capsule with flat base and acute to mucronate apex; about 7.0 mm long and 5.0 mm diameter; color at maturity nearest RHS 161C.

Seeds: Up to four; slightly flattened ellipsoid; about 3.5 mm long and 2.5 mm across and 2.0 mm thick; color nearest RHS 202A.

Hardiness and culture: The new plant grows best with plenty of moisture and adequate drainage; hardy to at least from USDA zone 3 through 8.

Disease and pest resistance: *Phlox* 'Amethyst Pearl' demonstrated the excellent powdery mildew resistance under conditions that would normally show symptoms.

I claim:

1. A new and distinct cultivar of hybrid *phlox* plant named *Phlox* 'Amethyst Pearl', as herein described and illustrated, especially suitable as a potted plant, for the garden, for attracting hummingbirds and butterflies, and for cut flower arrangements.

* * * * *